(12) United States Patent
Lages et al.

(10) Patent No.: US 6,506,368 B2
(45) Date of Patent: Jan. 14, 2003

(54) PROCESS FOR PRODUCING BLUE MICROCAPSULES

(75) Inventors: Rita Lages, Bodenwerder (DE); Frank Aickele, Holzminden (DE); Hubert Loges, Hoexter (DE); Arnold Machinek, Holzminden (DE)

(73) Assignee: Haarmann & Reimber GmbH, Holzminden (DE)

( * ) Notice: Subject to any disclaimer, the term of this patent is extended or adjusted under 35 U.S.C. 154(b) by 0 days.

(21) Appl. No.: 10/066,922

(22) Filed: Feb. 4, 2002

(65) Prior Publication Data

US 2002/0159957 A1 Oct. 31, 2002

(30) Foreign Application Priority Data

Feb. 9, 2001 (DE) .......................... 101 06 446

(51) Int. Cl.⁷ .............................. A61K 7/16; A61K 9/50
(52) U.S. Cl. ......................... 424/49; 424/490
(58) Field of Search .......................... 424/490

(56) References Cited

U.S. PATENT DOCUMENTS

| 3,341,466 A | | 9/1967 | Brynko et al. | 252/316 |
|---|---|---|---|---|
| 3,864,275 A | | 2/1975 | Kan et al. | 252/316 |
| 3,893,933 A | | 7/1975 | Brown | 252/62.1 |
| 3,957,964 A | * | 5/1976 | Grimm | 424/49 |
| 4,071,614 A | * | 1/1978 | Grimm | 424/49 |
| 4,348,378 A | * | 9/1982 | Kosti | 424/49 |
| 4,459,277 A | * | 7/1984 | Kosti | 424/49 |
| 5,169,975 A | * | 12/1992 | Schmitt et al. | 560/26 |
| 5,237,769 A | * | 8/1993 | Yamato et al. | 428/290 |
| 5,278,693 A | * | 1/1994 | Theiste et al. | 359/272 |
| 5,700,449 A | | 12/1997 | Katayama et al. | 424/49 |
| 6,046,177 A | * | 4/2000 | Stella et al. | 514/58 |
| 6,153,219 A | | 11/2000 | Creeth et al. | 424/451 |
| 6,287,542 B1 | * | 9/2001 | Bernard et al. | 424/49 |

FOREIGN PATENT DOCUMENTS

| GB | 1381444 | 1/1975 |
|---|---|---|
| WO | 00/48560 | 8/2000 |

OTHER PUBLICATIONS

Merck Index 12$^{th}$ Ed Entry 8251 Quinizarin Green (D&C Green #6)Entry 4581 Guaiazulene Blue Solution Gives Blue Green PPT, Blue Oil, Anti Inflammatory, 1996.*

* cited by examiner

*Primary Examiner*—Shep K. Rose
(74) *Attorney, Agent, or Firm*—Joseph C. Gil; Noland J. Cheung

(57) ABSTRACT

The invention relates to a process for producing uniformly colored blue microcapsules, using oil-soluble dyes.

2 Claims, No Drawings

PROCESS FOR PRODUCING BLUE MICROCAPSULES

FIELD OF THE INVENTION

The invention relates to a process for producing uniformly colored blue microcapsules using oil-soluble colors. These capsules are preferably used in the cosmetics industry and oral hygiene.

The present invention describes the encapsulation of a mixture of an oil-soluble material and a color, the resulting capsules being a blue to dark blue color. The preferred encapsulation method here is coacervation, preferably gelatine and gum arabic being used as coating material. Preferably, the resultant capsules which have a colorless transparent shell and a blue core are incorporated into products in the oral hygiene sector.

BACKGROUND OF THE INVENTION

Processes for producing microcapsules are known from the literature, as described, for example, in U.S. Pat. No. 3,341,466.

GB-A-1 381 444 discloses the teaching that microcapsules having a transparent shell comprising an oil and a color or a color suspension can be incorporated into toothpastes and these microcapsules then give a highly speckled or spotted or dotted appearance. In this case, the oily material serves principally as solvent or vehicle for the color.

EP-A-711 544 describes a toothpaste which uses capsules comprising agar as main constituent of the coating material. The capsules in this case have an average size of 0.3 to 3 mm.

A specific form of encapsulation for oral hygiene products is described in WO 99/59535, the aspects of stability of the capsules in the presence of surface-active substances, and of foam formation being of primary importance there.

WO 00/48560 relates to the encapsulation of a mixture of a liquid oil and a copper-chlorophyll extract. Preferably, these green microcapsules are used in oral hygiene products. Typical oils are sunflower seed oil or paraffin oil.

Usually, the above-mentioned microcapsules are produced by means of coacervation and the oil core is, if appropriate, colored. To prepare blue capsules there are, in principle, two possibilities.

If the shell of the capsules is made using a water-soluble color, decolorizing of the capsules occurs due to what is termed bleeding of the color, or due to instability of the color in the preparation or formulation of the formulated product to be used.

If the oil-soluble, that is to say lipophilic core of the capsule is colored, oil-soluble colors or colored pigments come into consideration for this type of coloring. When colored pigments are used, the problem of sedimentation very frequently occurs, that is to say the color is not homogeneously distributed in the capsule and results in the visual impression that the capsules are only half filled.

Satisfactory coloring of capsules with the color "blue" using dyes permitted in cosmetics has not succeeded to date, because there are only a few blue, oil-soluble dyes permitted for cosmetics.

Currently, there is no possibility for overcoming the problems described for producing blue capsules in the cosmetics sector. In the list of dyes there is no oil-soluble dye which is directly described as "blue".

SUMMARY OF THE INVENTION

It is therefore an object to produce microcapsules having a lipophilic core (core material), blue coloration of the core and transparent shell, with the dye used being an oil-soluble dye permitted in cosmetics.

Two oil-soluble dyes have now been found using which a blue coloration of the lipophilic core of the capsules is possible, the finished microcapsule having the required color stability and displaying neither sedimentation nor bleeding of the color.

The invention therefore relates to a process for producing blue microcapsules by encapsulating a mixture of a lipophilic core material and an oil-soluble dye, characterized in that the dye used is D&C Green No. 6 or guaiazulene or a mixture of these two dyes.

DETAILED DESCRIPTION OF THE INVENTION

First, guaiazulene (7-isopropyl-1,4-dimethylazulene) is proven to be a suitable dye according to the invention; second D&C Green No. 6 (1,4-bis(4-methylphenyl)amino)-9,10-anthracenedione; 1,4-p-toluidino-anthraquinone; C.I. 61565). The latter is particularly surprising, since this is listed as a green oil-soluble dye in the dye lists.

Both substances are commercially available dyes.

The dyes, depending on the intensity and depth of blue coloration desired, are added to the core material at 0.02% to 2%, preferably at 0.05% to 1.5%, more preferably 0.1% to 1% and most preferably at 0.1% to 0.5%. The percentages are by weight and are based on the amount of core material used.

Encapsulation materials, which are typically used which may be mentioned by way of example are: cyclodextrins, gum arabic, gelatin, casein, albumin, fibrinogen, xanthan gum, soluble peptides, sodium alginate, carboxymethyl cellulose, polyvinylpyrrolidones and other natural or synthetic polymeric materials. Preferably, the encapsulation materials are additionally crosslinked. The crosslinking can be inherent to the encapsulation material or can be induced by adding crosslinkers, for example glutaraldehyde.

Encapsulation can be performed by methods known per se and described in the literature. Preference in the present inventive process is given to coacervation.

In the present inventive process, preferably mixtures of gum arabic and gelatin are used, more preferably here a mixture ratio of 50%:50% by percent by weight. Final crosslinking with a crosslinker, preferably glutardialdehyde, is advantageous in order to achieve the desired hardness of the capsules.

The production process can be carried out as follows, for example:

The mostly liquid core material is mixed with the dye. This mixture is then introduced into an aqueous solution of the shell material, preferably comprising gelatin, at 40–60°. Then, if appropriate, a further shell material can be added, preferably gum arabic. The aqueous solution, can, if required, be admixed with a stabilizer or preservative. Preference is given to potassium sorbate. This emulsion is adjusted to a pH in the range 3.8to 4.8, preferably a pH from 4.0 to 4.5. The coacervates formed in this case, that is to say the colored liquid core material is enclosed by a film of shell material and water, with the microcapsules forming. After cooling, usually to temperatures below 15° C., a crosslinker, preferably glutardialdehyde, can be added to harden the shell.

The processing sequence can be modified in such a manner that the colored core material is added to an aqueous solution of gelatin and gum arabic and the pH is adjusted last.

If fish gelatin is used in the coacervation, the processing temperatures are lower, customarily 30 to 45° C.

After the production process, the capsules are present in the form of a slurry which can be further used as such. Depending on need and use, further treatments may follow. Thickeners, preferably carboxymethyl cellulose, preservatives and stabilizers, for example potassium sorbate and citrates, can be added to the slurry. Also, the slurry, as required, can be subjected to a drying, after which the microcapsules are present in free-flowing form.

The microcapsules have a transparent or translucent capsule shell and contain a blue liquid or a blue low-melting core material. Thus, the inventive produced capsules are highly visible in the formulated product to be used, for example, an oral hygiene product.

By means of careful matching of the production process conditions, properties, for example, hardness, size, wall thickness, color depth or stability of the capsules, can be critically influenced.

If the inventive blue capsules are incorporated into toothpastes, for example, the hardness of the capsules can be set by the inventive process in such a manner that the capsules are neither too hard to survive the cleaning operation, nor too soft to be destroyed during the production process of the oral hygiene product. Rather, in such a case, it is the aim that the capsules are gradually destroyed over the entire period of the cleaning operation and thus controlled release of the lipophilic material present in the capsules can take place.

Typically, the particle size of the blue capsules produced by the inventive process is in the range from 0.3 to 2.5 mm, preferably in the range from 0.5 to 1.8 mm and more preferably in the range from 0.8 to 1.2 mm. The particle size can be measured using customary methods, for example by sieving or microscopy.

The oil-soluble core material which is to be encapsulated according to the present invention can contain a single substance or a mixture. Some suitable core materials, which may be mentioned, by way of example, are listed below.

In addition to various edible oils, paraffin oils and silicone oils, the customary ingredients in the cosmetics and oral hygiene sectors can be used.

In particular, materials may be mentioned which have therapeutic, sensory, protective, personal-care or cosmetic effects. Proteins, keratin, collagen, casein, lecithin, sorbitol, antioxidants, phenol derivatives, antimicrobial agents, anti-inflammatory substances, caries-inhibiting substances, vitamins, enzymes, plant extracts, preservatives, pH-regulators, sweeteners, starch, flavorings and perfumes.

Particularly suitable as core material, for the purposes of the present invention, is the use of essential oils and extracts, tinctures and balsams, for example aniseed oil, basil oil, camphor oil, citronella oil, Eucalyptus citriodora oil, Eucalyptus oil, camomile oil, mint oil, lime oil, mandarin oil, clove oil, orange oil, peppermint oil, sage oil, thyme oil, vanilla extract, cinnamon bark oil and fractions thereof, and constituents isolated therefrom.

In addition, suitable substances as core material are those having a cooling refreshing effect in the oral, throat or nasal cavity. Those which may be mentioned, by way of example, are menthol, menthone, carboxamides, methone acetals, menthol carbonates, menthol succinates, 1,8-cineol (Eucalyptol), carvone, alpha-terpineol, thymol, methyl salicylate, 2'-hydroxypropiophenone. The optically active compounds can be used in enantiomerically pure form or as any mixture of the two enantiomers.

Applications of the inventive capsules in cosmetics and oral hygiene which may be mentioned are: creams, gels, foams, dispersions, chewing gums, pastilles and sweets.

More preference is given to the field of use of dental care products, in particular that of toothpastes, tooth creams, tooth gels.

The capsules are added, depending on the effect to be achieved, in the use in the oral hygiene sector at 0.05% to 5%, preferably at 0.2% to 3%, and more preferably at 0.5% to 1.5%. The percentages are by weight and are based on the finished product formulation or the total formulation.

The examples below illustrate the invention:

EXAMPLE 1

A mixture of peppermint oil and 0.1% D&C Green No. 6 was produced. This was added at 50° C. to an aqueous gelatin solution. This emulsion was then admixed with an aqueous solution of gum arabic. The pH of the mixture was then set to a pH of 4.5 by aqueous acetic acid solution, with stirring. The mixture was slowly cooled to room temperature and then glutardialdehyde was added. The supernatant solution was decanted off and the microcapsules were washed repeatedly with water. The capsules, thus produced, had a diameter of 0.6 to 1.5 mm. These microcapsules had a transparent shell and a blue core material.

EXAMPLE 2

A mixture of peppermint oil and 0.25% guaiazulene was produced. This was added at 50° C. to an aqueous gelatin solution. This emulsion was then admixed with an aqueous solution of gum arabic. The pH of the mixture was set to a pH of 4.5 by aqueous acetic acid solution with stirring. The mixture was slowly cooled to room temperature and then glutardialdehyde was added. The supernatant solution was decanted off and the microcapsules were washed repeatedly with water. The capsules thus produced had a diameter of 0.5 to 1.4 mm. These microcapsules had a transparent shell and a blue core material.

EXAMPLE 3

A transparent tooth gel having the following base formulation was produced, into which the blue capsules which were produced by different coloring methods or containing dyes were incorporated.

TABLE 1

| Ingredients | Parts by weight |
| --- | --- |
| 1. Sorbitol, 70% strength | 61.5 |
| 2. Distilled water | 11.4 |
| 3. Saccharin | 0.2 |
| 4. Sodium monofluorophosphate | 1.1 |
| 5. Trisodium phosphate | 0.1 |
| 6. Polyethylene glycol PEG 1500 (PEG 32) | 5.5 |
| 7. Abrasive silica gel | 8.0 |
| 8. Thickening silica gel | 8.0 |
| 9. Sodium carboxymethyl cellulose | 0.6 |
| 10. Sodium lauryl sulphate | 1.5 |
| 11. Flavorings | 1.0 |

TABLE 1-continued

| Ingredients | Parts by weight |
|---|---|
| 12. Blue capsules | 1.0 |
| 13. 4-Hydroxybenzoic acid methylester | 0.1 |

When capsules colored with the colored pigment Sicomet Blue P 74160 (copper phthalocyanin, C.I. 74160; CAS No. 147148) were used, the tooth gel, owing to the half-moon-like coloration of the capsules, had a non-uniform appearance which was not appealing. The finished tooth gel gave the impression of a faulty batch and did not have a rounded effect.

EXAMPLE 4

For the same dose of capsules produced in accordance with Example 1, it was found that the tooth gel had the optical impression of a homogeneous distribution of the blue capsules, and the capsules contributed harmoniously and refreshingly to the appearance.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. Oral hygiene products comprising blue transparent shell microcapsules produced by the process of encapsulating a mixture of a lipophilic core material and an oil-soluble dye, wherein said dye is D&C Green No. 6 or its mixture with guaiazulene.

2. Oral hygiene products according to claim 1, wherein said products are transparent toothpaste, tooth cream and tooth gel.

* * * * *